United States Patent
Cripe et al.

[11] Patent Number: 6,134,941
[45] Date of Patent: Oct. 24, 2000

[54] METHOD OF TESTING SENSORS AND APPARATUS THEREFOR

[75] Inventors: Jerry D. Cripe, Tempe; Theresa A. Maudie, Phoenix; Michael P. Menchio, Mesa; Dennis M. Stanerson, Scottsdale; David J. Monk, Mesa; James E. Kasarskis, Scottsdale; Charles L. Reed, Sr., Phoenix, all of Ariz.

[73] Assignee: Motorola, Inc., Schaumburg, Ill.

[21] Appl. No.: 09/046,024

[22] Filed: Mar. 23, 1998

[51] Int. Cl.[7] .......................... G01M 19/00; G01N 37/00
[52] U.S. Cl. ............................................. 73/1.02; 73/865.6
[58] Field of Search .................... 73/865.6, 1.02

[56] References Cited

U.S. PATENT DOCUMENTS

| | | | |
|---|---|---|---|
| 3,504,278 | 3/1970 | Lyons | 73/865.6 |
| 4,570,876 | 2/1986 | Davis | 73/1.02 |
| 4,601,409 | 7/1986 | Di Regolo | 141/65 X |
| 4,791,822 | 12/1988 | Penny | 73/865.6 |
| 4,859,375 | 8/1989 | Lipisko et al. | 141/1 X |
| 5,465,271 | 11/1995 | Bengel | 73/865.6 X |
| 5,707,147 | 1/1998 | Kurkowski et al. | 73/865.6 X |

*Primary Examiner*—Thomas P. Noland
*Attorney, Agent, or Firm*—A. Kate Huffman

[57] ABSTRACT

An apparatus for testing sensors in a media includes a chamber portion (240) for holding the sensors, tanks (320, 340) for supplying the media to the chamber portion (240) and coupled in parallel to the chamber portion (240), a pressure generator (310) coupled to the tanks (320, 340), and a heat exchanger (323, 324) adjacent to the tanks (320, 340). The media is simultaneously heated to different temperatures and pressurized to different pressures in the tanks (320, 340). Then, the media is delivered from the tanks (320, 340) to the chamber portion (240), and the sensors detect the media at the different temperatures and pressures.

10 Claims, 2 Drawing Sheets

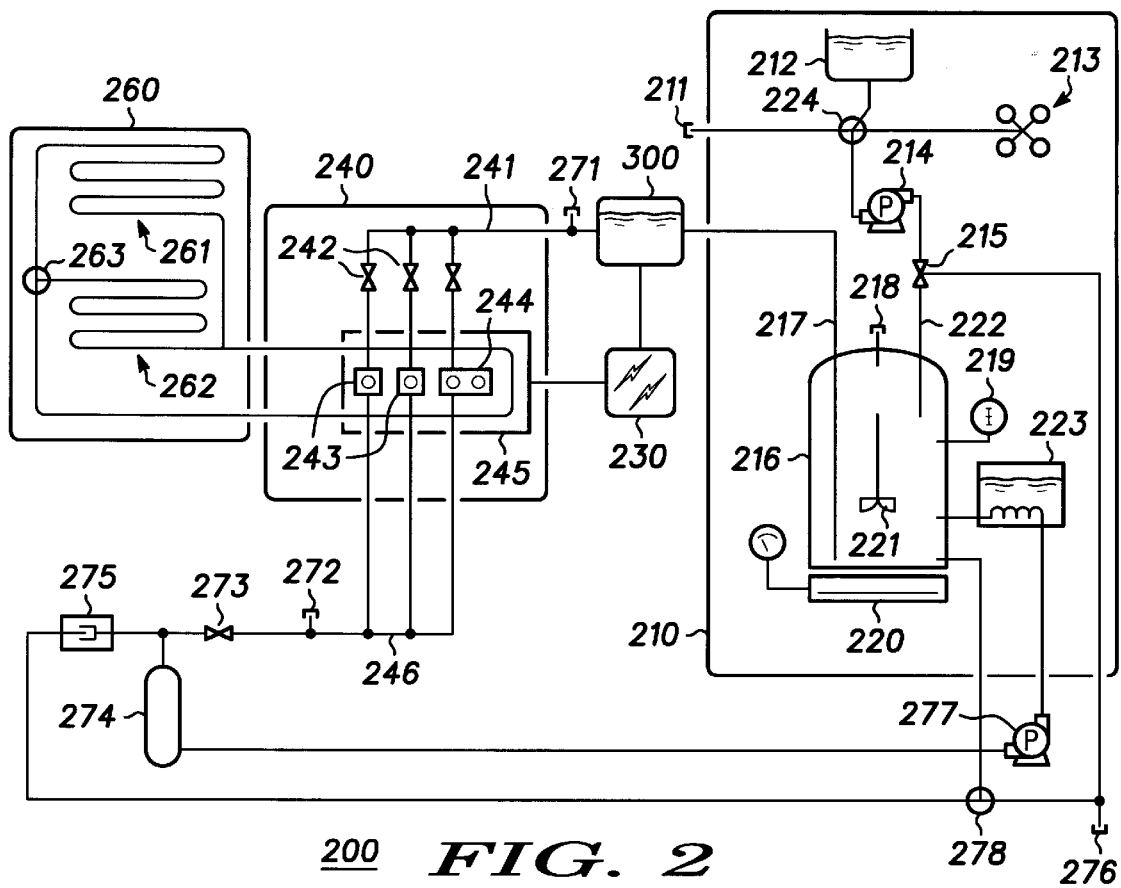
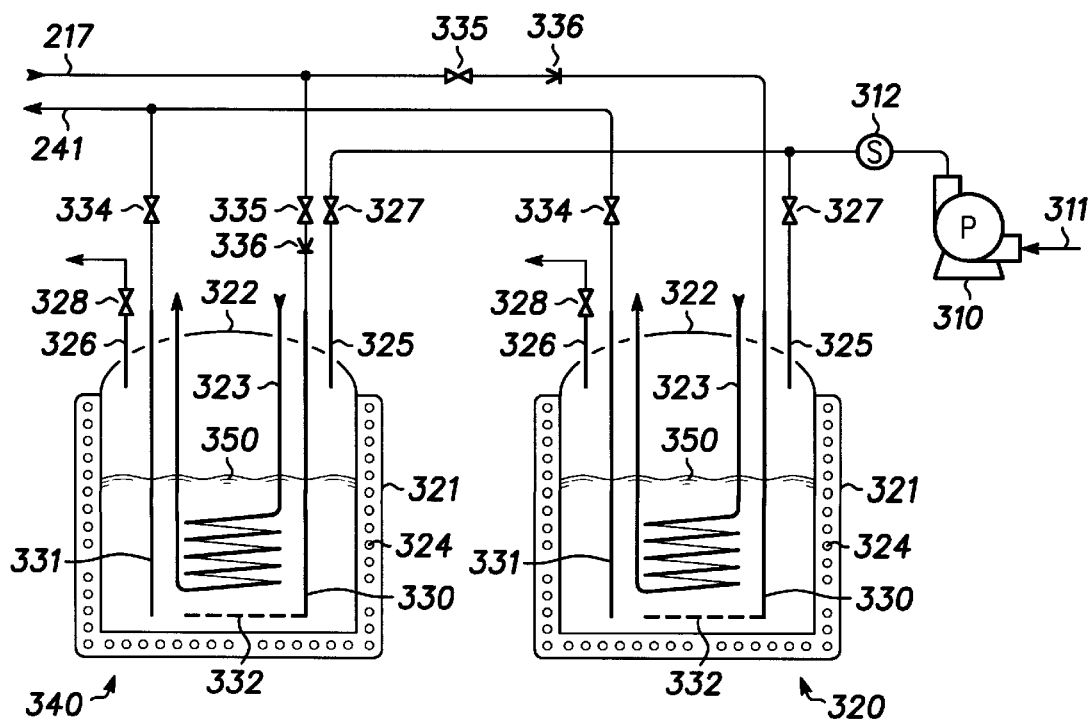

METHOD OF TESTING SENSORS AND APPARATUS THEREFOR

BACKGROUND OF THE INVENTION

This invention relates, in general, to electronic components, and more particularly, to methods and apparati for testing electronic components such as sensors.

Sensors can be used to detect qualities of harsh or hostile media including, but not limited to, combustible liquids, explosive vapors, radioactive liquids, organic liquids, and toxic solvents. The worldwide market for hostile media sensors is increasing each year. However, the conventional methods and apparati for functionally testing hostile media sensors under realistic operating conditions are extremely limited.

Most sensor test systems only operate at ambient pressure and temperature and cannot test sensors over a range of pressures and temperatures. A few systems are capable of testing sensors at elevated temperatures or pressures. However, the temperatures and pressures are essentially static because these prior art test systems cannot expose the sensors to rapid pressure fluctuations or dynamic temperatures changes. Therefore, the sensor testing performed under these prior art test systems does not accurately simulate realistic operating conditions. Furthermore, these prior art test systems cannot be safely operated while the electrically biased sensors are immersed in combustible, explosive, or flammable media such as gasoline.

Accordingly, a need exists for a safe method and apparatus for functionally testing sensors under realistic operating conditions including various harsh or hostile media, rapidly changing temperatures, and quick pressure fluctuations.

BRIEF DESCRIPTION OF THE DRAWINGS

FIG. 2 illustrates a simplified schematic view of an embodiment of a sensor test system in accordance with the present invention; and FIG. 3 illustrates a more detailed schematic view of an embodiment of a subsystem for generating and delivering pressurized and temperature controlled media in accordance with the present invention.

For simplicity and clarity of illustration, elements in the drawings are not necessarily drawn to scale, and the same reference numerals in different figures denote the same elements.

DETAILED DESCRIPTION OF THE DRAWINGS

Figure 1:
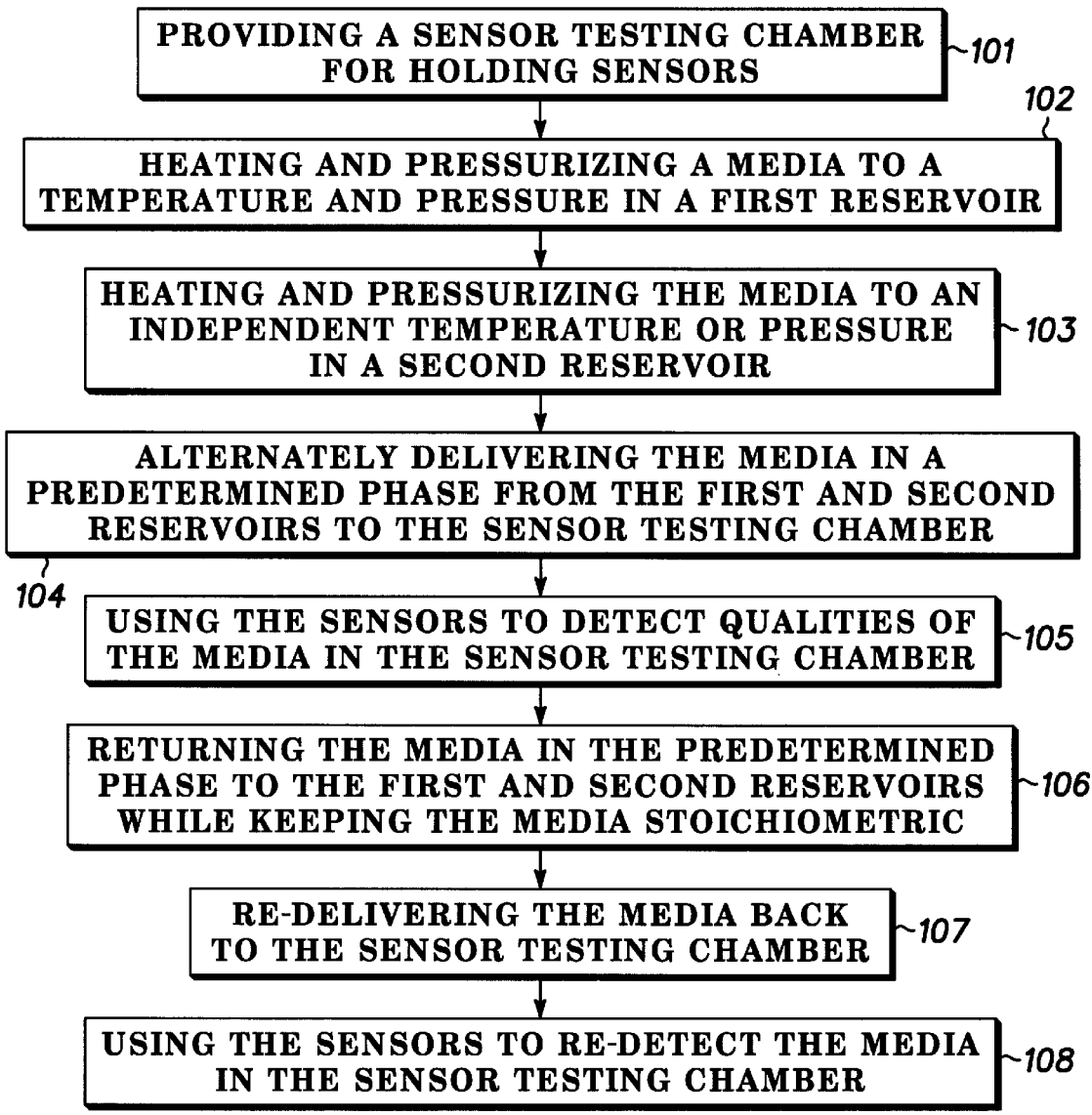
FIG. 1 illustrates a flow chart of a method for testing sensors in accordance with the present invention.

FIG. 1 illustrates a flow chart of a method 100 for testing sensors. Method 100 is used to test sensors in a media under realistic operating conditions. Method 100 includes a step 101 for providing a sensor testing chamber for holding sensors. The sensor testing chamber is described in more detail hereinafter with respect to FIG. 2.

Method 100 continues with steps 102 and 103 for heating and pressurizing a media in first and second reservoirs or tanks. Although steps 102 and 103 are listed sequentially in FIG. 1, steps 102 and 103 can also be performed simultaneously or in parallel with each other. Steps 102 and 103 can also cool the media to below room temperature and reduce the pressure of the media to below atmospheric pressure. The media can be heated or cooled to the same temperatures and pressurized to the same pressures in the first and second reservoirs. However, the media is preferably heated to different temperatures or pressurized to different pressures in the first and second reservoirs to simulate realistic operating conditions, as explained hereinafter in step 104. Examples of different types of media that can be used with method 100 include, but are not limited to, gases, liquids, solvents, acids, and bases.

Next, step 104 is performed. Step 104 delivers the media in a predetermined gaseous or liquid phase from the first and second reservoirs to the sensor testing chamber. Step 104 delivers a portion of the media from the first reservoir and subsequently delivers a portion of the media from the second reservoir. Alternating the media delivery between the first and second reservoirs permits rapid fluctuations in temperature, pressure, and media, which simulates realistic operating conditions for the sensors being tested.

Next, step 105 is performed. Step 105 uses the sensors to detect qualities of the media in the sensor testing chamber. Although steps 104 and 105 are listed sequentially in FIG. 1, steps 104 and 105 can also be performed simultaneously or in parallel with each other. In this embodiment of simultaneously performing steps 104 and 105, the sensors can be tested under dynamic pressure or temperature conditions, which simulates realistic operating conditions for the sensors and which provides more accurate performance and reliability data on the sensors.

Method 100 continues with a step 106 for returning the media in the gaseous or liquid phase to the first and second reservoirs. By returning the media in the same phase to the first and second reservoirs, the stoichiometry and other physical properties of the media are less likely to be altered during the testing of the sensors. However, even if the stoichiometry is altered by the process, method 100 can restore the stoichiometry by adding chemicals to the media, as explained in more detail in FIG. 2.

Next, step 107 is performed to re-deliver the media back to the sensor testing chamber. Step 107 permits the re-use of the media and simulates a closed system, which is a more realistic operating condition and which also reduces the amount of media required to test the sensors. Then, step 108 is performed to use the sensors to re-detect the qualities of the re-delivered media. Steps 107 and 108 can be similar to steps 104 and 105, respectively.

FIG. 2 illustrates a simplified schematic view of an apparatus or sensor test system 200 that can be used to carry out or perform method 100 of FIG. 1. System 200 of FIG. 2 includes, among other features, a filling stage or portion 210, a pressurized media delivery portion or subsystem 300, an electrical portion 230, a sensor testing chamber or portion 240, and a temperature controller or portion 260. Subsystem 300 is described in more detail hereinafter with respect to FIG. 3. However, other portions of system 200 are described in the following paragraphs. To facilitate the explanation of system 200, the system is described for use with a liquid phase media. Appropriate modifications can be made for gaseous phase media.

Sensor testing chamber or portion 240 includes an input line 241 which delivers the media from subsystem 300. Input line 241 can include a port 271 to permit sampling of the media for diagnostic purposes before the media is delivered to the sensors. Port 271 can also be used to add chemistries to the media in order to correct or alter the stoichiometry of the media.

Line 241 can be split into a plurality of feedlines, which are individually coupled to valves 242. Then, valves 242 can be coupled to individually isolatable compartments 243 and 244, in which the sensors being tested are located. Compartments 243 are for single or separate sensors while compartment 244 is for a plurality of sensors. As an example, the sensors can be pressure sensors, chemical sensors, or flow sensors. The sensors are held in a sensor block 245 while the sensing portion of the sensors are exposed to the media in compartments 243 and 244. Alternatively, the entire sensor can be exposed to the media. Sensor block 245 can support a single type of sensor or can simultaneously accommodate different types of sensors. As an example, block 245 can be used to simultaneously support a gasoline chemical sensor and a gasoline flow sensor. In this embodiment, two types of sensors can be simultaneously tested in the same media. If the sensor has a sensing diaphragm, block 245 can expose a single side or both sides of the sensing diaphragm to the media or various medias.

The media leaves compartments 243 and 244 through output lines 246, which can be merged into a single output line as illustrated in FIG. 2. Output lines 246 can include a port 272 to permit sampling of the media for diagnostic purposes after the media is exposed to the sensors. Output lines 246 can be separated from the rest of system 200 by a valve 273.

Temperature controller or portion 260 includes cooling coils 261 and heating coils 262. Coils 261 and 262 can be used to cool or heat sensor block 245, the media in compartments 243 and 244, the sensors, or all the above. A switch or three-way valve 263 can be used to select the use of either coils 261 or 262. Coils 261 and 262 are described in more detail hereinafter.

Electrical portion 230 is used to electrically bias, acquire data from, and operate the sensors held by sensor block 245. Electrical portion 230 also controls safety interlocks of system 200 and insures the safe operation of the entire system 200. Electrical portion 230 can include computers to graphically view the test results of the sensors in real time. Electrical portion 230 can also be used to operate temperature controller or portion 260 and subsystem 300, as explained in more detail hereinafter with respect to FIG. 3.

Valve 273 couples output lines 246 to the recirculation plumbing of system 200. As an example, valve 273 can be coupled to an optional bladder or accumulator 274, which can be used to contain excess or overflow media from compartments 243 and 244. If accumulator 274 is overfilled, then the media can escape through an expansion or regulator valve 275, through a switch or three-way valve 278, and exit system 200 through a drain 276. Drain 276 is a "smart drain" controlled or programmed to direct the media to different reservoirs depending upon, for example, the temperature, pressure, chemistry, or phase of the media. Valve 275 and drain 276 improve the safety of system 200.

Accumulator 274 is coupled to a pump 277, which returns the media to filling stage or portion 210. Portion 210 of system 200 includes a gas input line 211, a liquid cleaning source 212, and media sources 213, which are all coupled to a metering pump 214 through a switch 224. As an example, switch 224 can be safely operated by electrical portion 230. Line 211 and source 212 can be used to flush and clean the plumbing lines and tanks of system 200. As an example, line 211 can contain an inert gas such as nitrogen, and cleaning source 212 can be comprised of isopropyl alcohol.

Metering pump 214 is coupled to an input port 222 of a recirculation tank 216. Tank 216 can use a dynamic mechanical or magnetic mixer 221 to combine new or fresh media from media sources 213 with used media. The used media is pumped into tank 216 by pump 277, but pump 277 delivers the used media to a heating bath 223 before sending it to tank 216. Bath 223 is used to re-heat the used media to the temperature of the media already present in tank 216. The reduction in temperature gradients during the media mixing reduces temperature shock and maintains the stoichiometry of the media. Furthermore, the phase of the media in heating bath 223 and recirculation tank 216 is preferably the same to reduce the chance of changing the physical properties of the media during mixing of the media in tank 216.

If tank 216 is overfilled by media from bath 223 or media sources 213, valve 215 can be opened to permit the media to overflow to drain 276. A scale 220 underneath tank 216 or a level indicator 219 in tank 216 can be used as a feedback mechanism to trigger the opening of valve 215. Tank 216 also includes a nitrogen purge line 218 for reducing the pressure within tank 216 and an output line 217 coupled to subsystem 300.

FIG. 3 illustrates a more detailed schematic view of subsystem 300 for generating, supplying, and delivering pressurized and temperature controlled media to sensor testing chamber or portion 240 of FIG. 2. Subsystem 300 of FIG. 3 includes, among other features, reservoirs or tandem supply tanks 320 and 340, each of which are coupled in parallel to portion 240 of FIG. 2. Tank 320 includes an inner reservoir or tank 322 located inside an outer reservoir or tank 321. A media 350 is located in and contacts inner tank 322, but media 350 does not contact outer tank 321. This double-walled embodiment of tank 320 improves the safety of subsystem 300. As an example, tank 320 is an unfired pressure rated vessel, as classified by the American Society of Mechanical Engineers (ASME).

Tank 320 also includes heat exchangers 323 and 324 for heating media 350 within tank 320. Heat exchanger 323 is located in and adjacent to inner tank 322. Heat exchanger 324 is adjacent to both inner and outer tanks 322 and 321, but is located inside outer tank 321 and outside inner tank 322. Heat exchanger 323 contacts media 350 while heat exchanger 324 does not contact media 350. However, heat exchanger 324 still heats media 350 by heating the wall of tank 322. In an alternative embodiment, heat exchanger 323 or 324 can be removed from tank 320, leaving only one heat exchanger in tank 320. In another alternative embodiment, heat exchangers 323 and 324 can be separate heating elements of the same heat exchanger.

The temperature of heat exchangers 323 and 324 are controlled by electrical portion 230 of FIG. 2. Heat exchangers 323 and 324 should be able to cool or heat media 350 to temperatures ranging from about negative sixty-five degrees Celsius to about two hundred degrees Celsius. Heat exchangers 323 and 324 are preferably comprised of heated or cooled inert or fluorinated hydrocarbon chemicals circulated through pipes within tank 320. The use of inert chemicals improves the safety of subsystem 300 by reducing the possibility of igniting media 350 with sparks generated by conventional electric heaters. Heating coils 261 and cooling coils 262 of FIG. 2 are preferably similar to heat exchangers 323 and 324 for the same safety reasons.

Tank 320 further includes a pressure input port 325 and a pressure output or discharge port 326. The opening of input port 325 is preferably above the highest level of media 350 to reduce the agitation of media 350. This feature of port 325 may be modified if media 350 has a gaseous phase instead of a liquid phase. A controlled valve 328 coupled to discharge port 326 is used to reduce the pressure exerted on media 350 in tank 320. In one embodiment, valve 328 is coupled to drain 276 of FIG. 2.

Pressure input port 325 is coupled to a pressure generator 310 through a valve 327 and a high pressure monitor and regulator 312. Generator 310 has an output port coupled to regulator 312 and an input line 311 for a relatively inert gas such as, for example, argon, nitrogen, or krypton. The relatively inert gas is used to create pressure in tank 320 so that the gas will not mix or react with media 350. Instead, the gas will merely lay on top of media 350. In one embodiment, generator 310 is able to create a pressure ranging from atmospheric pressure to about one thousand four hundred kilopascals to permit the realistic functional testing of sensors. In the preferred embodiment, generator 310 is a multiplier or displacement pump. Tank 320 should be able to contain a pressure that is at least twice as great as the maximum pressure generated by generator 310 to maintain safe operation of subsystem 300.

Tank 320 additionally includes a media input port 330 and a media output port 331. Input port 330 is coupled to a throttle valve 335 and a check valve 336 to control the pressure in sensor testing chamber or portion 240 of FIG. 2. As an example, valves 335 and 336 can be part of an adjustable compumotor throttle output valve. Valve 335 is coupled to output line 217 of recirculation tank 216 in FIG. 2. The opening of input port 330 is preferably below the surface of media 350 in tank 320 and preferably includes a sintered porous diffuser plate 332 in order to reduce the amount of agitation of media 350 in tank 320. To reduce gas bubbles in media 350, the opening of output port 331 is also preferably below the surface of media 350. However, output port 331 is preferably not too close to the bottom of tank 322 so that any contaminants such as sediment in tank 322 are not fed into output port 331. Output port 331 is coupled to valve 334, which is coupled to input line 241 of portion 240 in FIG. 2.

As illustrated in FIG. 3, tank 340 is nearly identical to tank 320. Pressure generator 310 is preferably independently coupled to each of tanks 320 and 340 such that the pressure in tank 320 can be different from the pressure in tank 340. Independent control of valves 327 and 328 of tanks 320 and 340 enables the creation of different pressures within tanks 320 and 340. Similarly, the independent control of heat exchangers 323 and 324 in tanks 320 and 340 enables the creation of different temperatures within tanks 320 and 340. Therefore, tanks 320 and 340 can be used to simultaneously provide different pressures and different temperatures for media 350. Additionally, the independent control of valves 334 of tanks 320 and 340 provides independent coupling of tanks 320 and 340 to sensor testing chamber or portion 240 of FIG. 2. The independent control of valves 334 of tanks 320 and 340 also enables fast dynamic changes in temperature and pressure of media 350 that is delivered to the sensors in portion 240 of FIG. 2.

Therefore, an improved method and apparatus for testing sensors is provided and overcomes the disadvantages of the prior art. The method and apparatus are capable of functionally testing sensors under a wide range of operating conditions, including immersion in different types of media and exposure to rapid changes or ramps in pressure, temperature, and phases for a given media. The method and apparatus also allow for pressure correction and for continuous testing even after certain sensors fail by isolating certain blocks of sensors. The method and apparatus of testing is also suitable for use with control samples that can be exposed to different temperatures, pressures, or media compared to the samples or sensors being tested. The data from the control samples is used to evaluate the data from the tested samples. The method and apparatus are also safely compatible with harsh or hostile media, including flammable or explosive media. The use of tandem media tanks facilitates dynamic temperature and pressure testing and also permits continuous test system operation when one of the tandem tanks must be refilled or replaced.

While the invention has been particularly shown and described mainly with reference to preferred embodiments, it will be understood by those skilled in the art that changes in form and detail may be made without departing from the spirit and scope of the invention. For instance, the numerous details set forth herein such as, for example, specific chemical compositions, pressure ranges, and temperature ranges are provided to facilitate the understanding of the present invention and are not provided to limit the scope of the invention. As an additional example, various valves, feed lines, and electrical connections can be added to system 200 to provide additional functionality. Moreover, system 200 can be used to test non-sensor electronic components for reliability, corrosion resistance, or the like. Similarly, non-harsh or non-hostile media, such as inert media, can also be used with system 200. Additionally, while only two tanks are illustrated in subsystem 300 of FIG. 3, more than two tanks can be used to provide an even greater range of dynamic testing. Moreover, the safety and temperature stability of system 200 and subsystem 300 can be further improved by, for example, using plumbing lines that are double contained with a fluorinated hydrocarbon outer jacket.

Accordingly, the disclosure of the present invention is not intended to be limiting. Instead, the disclosure of the present invention is intended to merely be illustrative of the scope of the invention, which is set forth in the following claims.

What is claimed is:

1. An apparatus for testing sensors in a media comprising:
a chamber comprising an individual isolatable compartment, each compartment holding a sensor;
reservoirs for supplying the media to the chamber and coupled in parallel to the chamber;
a pressure generator coupled to the reservoirs; and
a heat exchanger adjacent to the reservoirs.

2. The apparatus of claim 1 wherein the pressure generator is independently coupled to each of the reservoirs.

3. The apparatus of claim 1 wherein the heat exchanger further comprises a separate and independently controllable heat exchanging element for each of the reservoirs.

4. The apparatus of claim 3 wherein each of the separate and independently controllable heat exchanging elements are located inside the reservoirs.

5. The apparatus of claim 1 further comprising a smart drain coupled to the reservoirs and the chamber.

6. The apparatus of claim 1 further comprising a port for maintaining stoichiometry of the media wherein the port is coupled to the chamber and the reservoirs.

7. An apparatus comprising:
a test chamber for holding and electrically operating a plurality of sensors and for holding a media capable of being detected by the plurality of sensors and having a test chamber input and a test chamber output;
a first tank having an inner tank for holding the media, having a first tank input coupled to the test chamber output, having a first tank output, having a first tank pressure discharge port, having a first tank pressure input port, and having an outer tank wherein the inner tank is located inside the outer tank;

a second tank for supplying the media, having a second tank input coupled to the test chamber output, having a second tank output, having a second tank pressure discharge port independently controlled from the first tank pressure discharge port, and having a second tank pressure input port;

a first media valve coupling the first tank output to the test chamber input;

a second media valve coupling the second tank output to the test chamber input and independently controlled from the first media valve;

a first heat exchanger in the inner tank of the first tank;

a second heat exchanger in the second tank and independently controlled from the first heat exchanger;

a pressure generator having a pressure output port;

a first pressure valve coupling the pressure output port to the first tank pressure input port; and a second pressure valve coupling the pressure output port to the second tank pressure input port and independently controlled from the first pressure valve.

8. The apparatus of claim 7 further comprising:

a third heat exchanger; and a fourth heat exchanger, wherein
the third heat exchanger is in the outer tank and wherein the media devoids contacting the outer tank and the third heat exchanger, and wherein the second tank further comprises:
a second inner tank for holding the media and the second heat exchanger; and
a second outer tank for holding the second inner tank and the fourth heat exchange wherein the media devoids contacting the second outer tank and the fourth heat exchanger.

9. The apparatus of claim 8 further comprising:

a first diffuser coupled to the first tank input; and a second diffuser coupled to the second tank input.

10. The apparatus of claim 7 wherein the test chamber further comprises a separate chamber for each of the plurality of sensors.

* * * * *